United States Patent [19]
Chu

[11] Patent Number: 5,187,982
[45] Date of Patent: Feb. 23, 1993

[54] VIBRATION CONTROLLED EXPERIMENTING DEVICE PROVIDED WITH A MOTOR WITH AN IMBALANCED ROTOR

[76] Inventor: Cheng Chu, No. 1, Ln. 24, Kuei-Feng St., Tai-Shan Hsiang, Taipei Hsien, Taiwan

[21] Appl. No.: 691,990

[22] Filed: Apr. 26, 1991

[51] Int. Cl.⁵ .............................................. G01N 3/32
[52] U.S. Cl. ...................................... 73/666; 73/667; 73/672
[58] Field of Search ............... 73/662, 663, 665, 666, 73/667, 668, 672

[56] References Cited

U.S. PATENT DOCUMENTS

| | | | |
|---|---|---|---|
| 2,305,783 | 12/1942 | Heymann et al. | 73/666 |
| 2,366,342 | 1/1945 | Lazan | 73/672 |
| 2,906,991 | 9/1959 | Camp | 73/662 |
| 3,555,892 | 1/1971 | Hizume et al. | 73/672 |
| 4,069,706 | 1/1978 | Marshall et al. | 73/666 |
| 4,180,458 | 12/1979 | Shahan | 73/662 |
| 4,364,275 | 12/1982 | LaMar | 73/672 |
| 4,389,883 | 6/1983 | Köder et al. | 73/668 |
| 4,709,362 | 11/1987 | Cole | 73/667 |
| 4,825,692 | 5/1989 | Rohs et al. | 73/662 |
| 5,033,302 | 6/1991 | Mönch | 73/672 |

FOREIGN PATENT DOCUMENTS

| | | | |
|---|---|---|---|
| 1057566 | 9/1966 | Australia | 73/672 |
| 1224966 | 9/1960 | Fed. Rep. of Germany | 73/672 |

*Primary Examiner*—Hezron E. Williams
*Assistant Examiner*—Howard Wisnia
*Attorney, Agent, or Firm*—Bacon & Thomas

[57] ABSTRACT

A controlled vibration experiment device having a vibration model structure to simulate actual mechanical vibration and to monitor and analyze the vibration by a computer monitor. The device has a base plate, a supporting frame, a T-shaped sliding rail, a servo motor, a connecting piece and a decoder with a rotatable shaft. The vibration produced is changed to an electrical signal and input to the computer to display the various type of waveforms. The vibration phenomena is then analyzed by a computerized monitor.

2 Claims, 3 Drawing Sheets

VIBRATION CONTROLLED EXPERIMENTING DEVICE PROVIDED WITH A MOTOR WITH AN IMBALANCED ROTOR

BACKGROUND OF THE PRESENT INVENTION

The present invention relates to a vibration controlled experimenting device, in particular, to a vibration model system to simulate the actual vibrating condition which is monitored and analyzed by means of a computer monitor.

In the field of automatic control systems, the two most popular ways to control a body are mass spring damping in the mechanical system and a DC servo motor in the electrical system. The DC servo motor controlled system is well-known and popular in the state-of-the-art, but the mass spring damping controlled system is comparatively not common. However, this system can be found in the suspension systems of motorcycles and cars, and also can be found in washing machines, electric fans, spring suspension beds, and other machinery used in the electrical and chemical industries.

SUMMARY OF THE INVENTION

Accordingly, it is an object of the present invention to provide a controlled vibration experimenting device which simulates vibration phenomena in a mechanical system, wherein a computer control and monitor are used to determine the vibration simulation.

It is another object of the present invention to provide a controlled vibration experimenting device, wherein a centrifugal member is provided thereon to allow various types of vibration experiments.

It is another object of the present invention to provide a controlled vibration experimenting device, wherein the device allows the experimenting with the principles of static, dynamic, and natural frequency and resonance phenomena and the control system.

BRIEF DESCRIPTION OF THE DRAWINGS

The present invention will be further explained with reference to the annexed drawings, wherein.

DETAILED DESCRIPTION OF THE INVENTION

While this specification concludes with claims particularly pointing our and distinctly claiming that which is considered to be the invention, it is believed that the invention can be better understood from a reading of the following detailed description of the invention.

Figure 1:
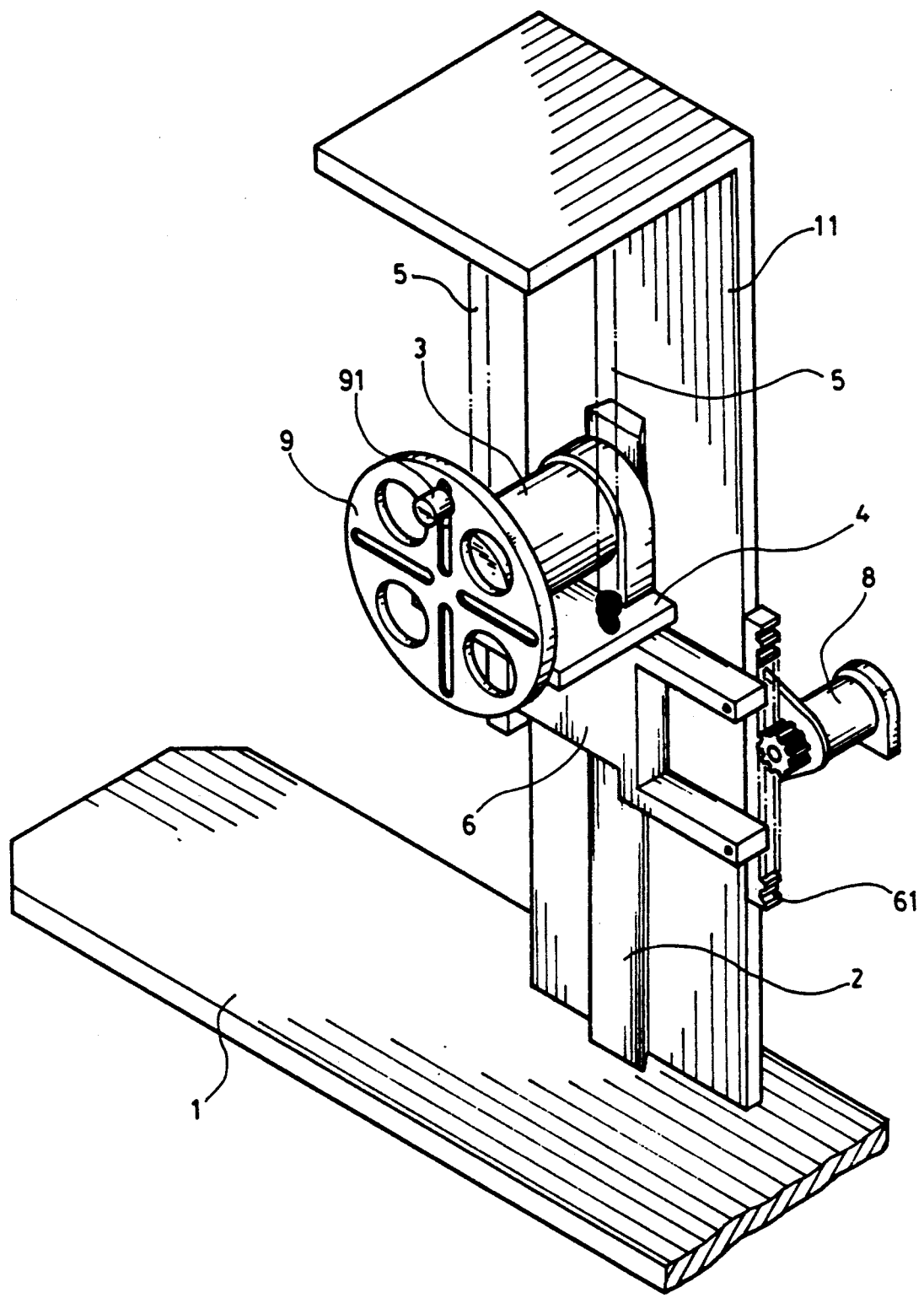
FIG. 1 is a perspective view of a controlled vibration experimenting device in accordance with the present invention.
Figure 2:
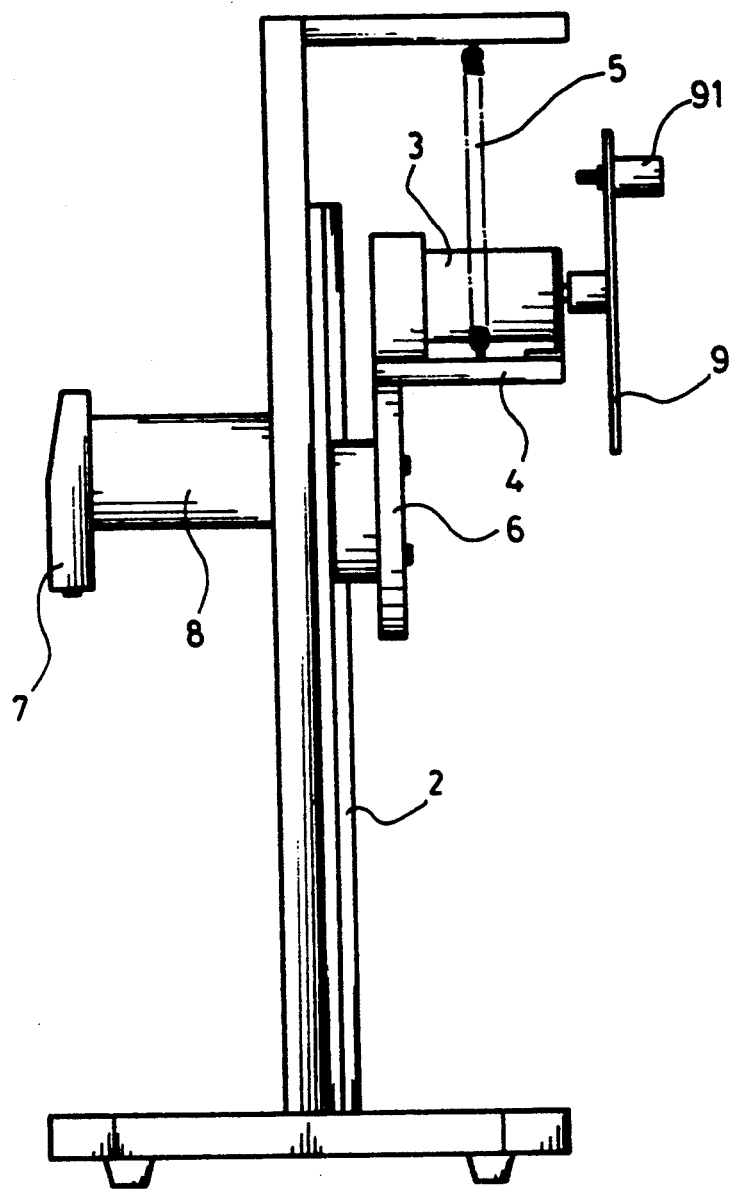
FIG. 2 is a side view of the controlled vibration experimenting device in accordance with the present invention.
Figure 3:
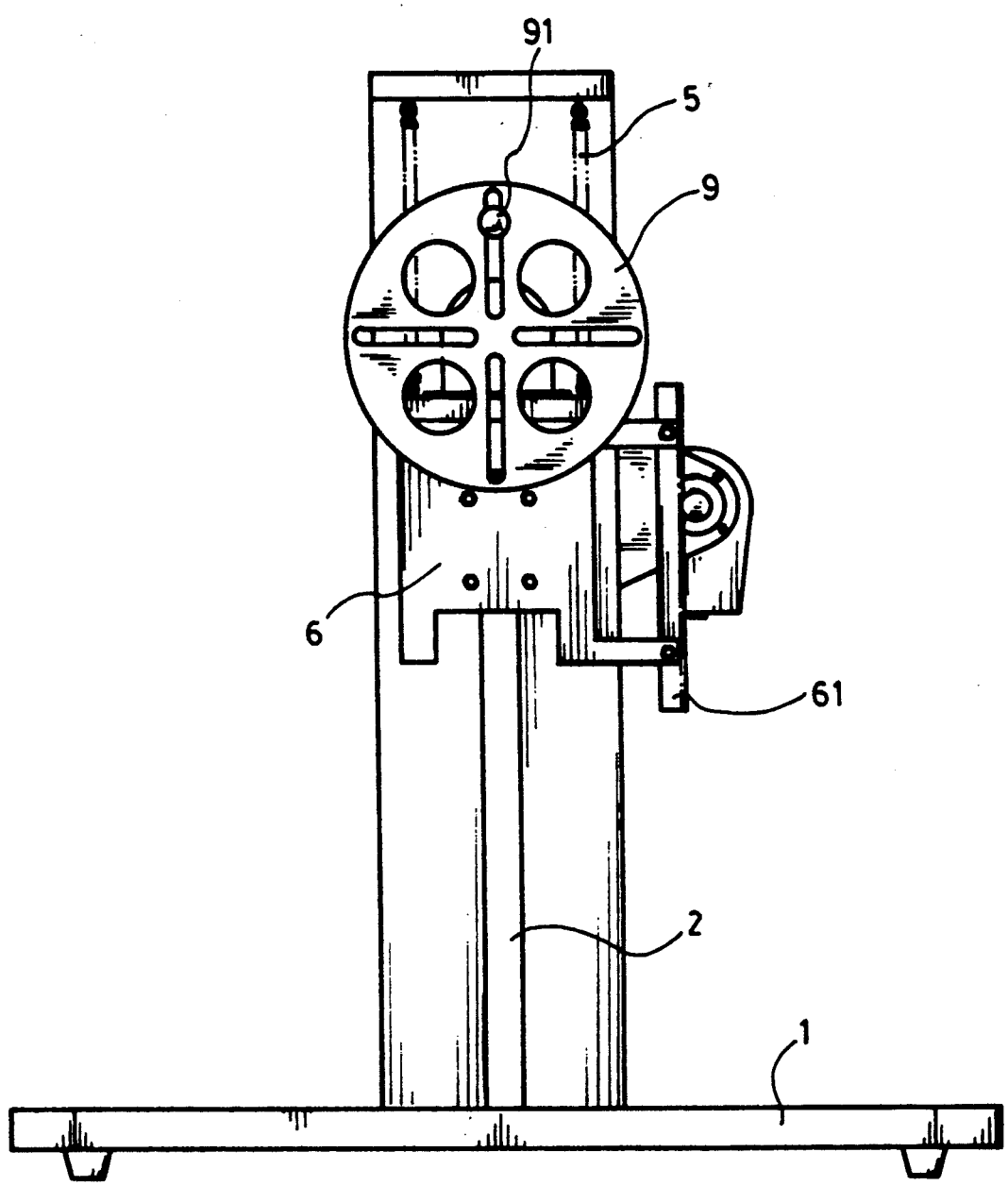
FIG. 3 is the front view of the controlled vibration experimenting device in accordance with the present invention.

Referring to the figures, in particular, to FIG. 1, a controlled vibration experimenting device is shown. The controlled vibration experimenting device in accordance with the present invention is a vibration model structure which is used to simulate an actual mechanical vibration and which then monitors and analyzes the waveform produced by means of a computerized monitor. In accordance with the present invention, the experimenting device comprises (a) a base 1; (b) a supporting frame 11 perpendicularly mounted onto the base 1, having an L-shaped portion at the top end thereof; (c) a T-shaped sliding rail 2 disposed on said base 1 and extending parallel with the supporting frame 11; (d) a connecting plate 6 being connected by means of a linear bearing so as to be moveable along said T-shaped rail 2 in a vertical direction, a geared strip 61 being provided along the one section of the edge of the supporting frame 11; (e) a servo motor 3 being mounted to the top section of the connecting plate 6 by a fixing seat 4 and being suspended from the L-shaped portion of said supporting frame 11 by a plurality of springs; (f) a rotating disc 9 being connected to the rotating shaft of the servo motor 3 by a connecting head, a centrifugal member 91 being provided on said disc; whereby the disc 9 is provided with a plurality of radial slots and the centrifugal member 91 is movable within these slots; and (g) a decoder being connected to the servo motor 3, by means of the engagement of the geared strip 61 of the connecting plate 6 with a shaft of a servo motor 8, the displacement of the geared strip 61 being converted to electric signal.

In operation, the servo motor 3 will rotate at a desired speed. Due to the centrifugal member 91 on the rotating disc 9, a vibration phenomena is produced which will achieve resonance. Such a resonance is transmitted to the connecting plate 6 through the motor mounting seat 4. The connecting plate 6 vibrates up and down along the T-shaped rail 2 which displaces the geared strip. The displacement of the strip 61 changes into a rotating signal through its connection with the servo motor 8. The mechanical signal of this vibration is changed into an electric signal by means of a known decoder or transducer 7. A computer (not shown) which is connected to the decoder or transducer 7 will display the resonance frequency on a monitor based on the electric signal. The computer may calculate an output with various data based on the input signal and variables and based on a translation function. Different frequencies and forms are obtained with respect to the input variables such as the speed of rotation of the motor 3, the biasing force of the rotating disc, the spring force, etc.

While only one embodiment of the present invention has been shown and described herein, it will be appreciated that modifications thereof may still be readily made thereto by those skilled in the art. Therefore, it is intended by the appended claims to cover the modifications alluded to herein as well as all other modifications which fall within the true spirit and scope of our invention.

I claim:

1. A controlled vibration experimenting device having a vibration model structure to simulate actual mechanical vibration, comprising,
   (a) a base;
   (b) a supporting frame perpendicularly mounted onto the base, having an L-shaped portion at the top end thereof;
   (c) a T-shaped sliding rail disposed on said base;
   (d) a connecting plate moveable along said T-shaped rail in a generally vertical direction;
   (e) a geared strip attached to the connecting plate;
   (f) a servo motor mounted to the connecting plate by a fixing seat;

(g) a plurality of springs suspending the connecting plate from the L-shaped portion of said supporting frame;
(h) a disc connected to the a rotatable shaft of the servo motor by a connecting head;
(i) a centrifugal member mounted on said disc; and,
(j) decoder means operatively associated with the connecting plate by a gear engaging the geared strip so as to convert the movement of the geared strip into an electric signal.

2. A controlled vibration experimenting device as set forth in claim 1, further comprising a plurality of radial slots provided in the disc whereby the centrifugal member may be mounted on the disc along said slots for the adjustment with respect to the centrifugal force.

* * * * *